(12) United States Patent
Davis

(10) Patent No.: US 8,434,869 B2
(45) Date of Patent: May 7, 2013

(54) AUTOMATED LOCKING APPARATUS FOR A SLIT LAMP

(76) Inventor: Andrew P. Davis, Bellevue, WA (US)

(*) Notice: Subject to any disclaimer, the term of this patent is extended or adjusted under 35 U.S.C. 154(b) by 0 days.

(21) Appl. No.: 12/829,826

(22) Filed: Jul. 2, 2010

(65) Prior Publication Data
US 2011/0001931 A1 Jan. 6, 2011

Related U.S. Application Data

(60) Provisional application No. 61/270,105, filed on Jul. 3, 2009.

(51) Int. Cl.
G02C 5/16 (2006.01)
G02C 5/00 (2006.01)

(52) U.S. Cl.
USPC .................................. 351/214; 351/245

(58) Field of Classification Search ........... 351/200–246
See application file for complete search history.

(56) References Cited

U.S. PATENT DOCUMENTS

| | | | | |
|---|---|---|---|---|
| 4,477,159 A * | 10/1984 | Mizuno et al. | ........... | 351/221 |
| 4,838,678 A | 6/1989 | Hubertus | ........... | 351/205 |
| 5,000,563 A | 3/1991 | Gisel et al. | ........... | 351/245 |
| 5,321,446 A * | 6/1994 | Massig et al. | ........... | 351/214 |
| 5,387,952 A | 2/1995 | Byer | ........... | 351/208 |
| 5,717,480 A | 2/1998 | Brooks et al. | ........... | 351/221 |
| 6,283,596 B1 * | 9/2001 | Yoshimura et al. | ........... | 351/214 |
| 6,575,575 B2 * | 6/2003 | O'Brien et al. | ........... | 351/245 |
| 6,715,878 B1 | 4/2004 | Gobbi et al. | ........... | 351/243 |
| 7,377,644 B2 * | 5/2008 | Davis | ........... | 351/208 |
| 7,425,067 B2 | 9/2008 | Warden et al. | ........... | 351/205 |
| 7,549,748 B2 | 6/2009 | Davis | ........... | 351/208 |
| 7,744,219 B2 | 6/2010 | Davis | ........... | 351/221 |
| 2005/0286019 A1 | 12/2005 | Wiltberger et al. | ........... | 351/221 |
| 2006/0050229 A1 | 3/2006 | Farberov | ........... | 351/219 |
| 2007/0257772 A1 * | 11/2007 | Marcelle et al. | ........... | 340/5.64 |
| 2008/0044063 A1 | 2/2008 | Friedman et al. | ........... | 382/117 |

FOREIGN PATENT DOCUMENTS

| | | |
|---|---|---|
| WO | 2005047572 | 2/2005 |
| WO | 2005094667 | 10/2005 |
| WO | 2006041625 | 4/2006 |
| WO | 2007067986 | 6/2007 |

* cited by examiner

*Primary Examiner* — Mohammed Hasan
(74) *Attorney, Agent, or Firm* — Lowe Graham Jones PLLC

(57) ABSTRACT

An apparatus mounted proximate to or on a base of a slit lamp illumination unit operates to automatically lock or secure the illumination unit in a stationary position after each eye examination and further operates to unlock it just before each examination. The apparatus may take the form of a threaded rod that replaces the conventional thumbscrew. The threaded rod is rotated by a motor, which receives instructions from a controller, both located within a housing. A touch sensor on the housing communicates with the controller to activate the locking or unlocking of the threaded rod and may also provide a signal to a transceiver for powering the illumination unit ON or OFF.

18 Claims, 3 Drawing Sheets

AUTOMATED LOCKING APPARATUS FOR A SLIT LAMP

PRIORITY CLAIM

This application claims the benefit of U.S. Provisional Application No. 61/270,105 filed on Jul. 3, 2009, the subject matter of which is incorporated herein by reference in its entirety.

FIELD OF THE INVENTION

This invention relates generally to a non-manual (i.e., automatic) locking apparatus for a slit lamp, and more specifically to an automated locking apparatus that replaces a conventional, manual thumbscrew.

BACKGROUND OF THE INVENTION

A slit lamp, also called a biomicroscope, is used for examining a human eye. The slit lamp includes a high-intensity light source that can be focused to shine a thin sheet of light into the eye for examination of the anterior and posterior segments of the eye. A slit-lamp examination provides stereoscopic magnified view of the eye structures in detail, enabling anatomical diagnoses to be made for a variety of eye conditions. One type of slit lamp is described in U.S. Pat. No. 6,283,596 while another type is described in U.S. Pat. No. 7,549,748.

FIG. 1 shows a partial view of a conventional slit lamp 10 that moves fore-aft and side-side relative to a surface 12, such as a platform or table. The slit lamp 10 moves in forward or aft translational direction 13 on an axle 14, which is coupled to wheels 15 that are configured to mesh or engage with a track 16. Accurate positioning of the slit lamp 10 is generally achieved with a joystick 17. The wheels 15 may be covered by end caps 18, which may or may not include the tracks 16. The end caps 18 may be fixed to the stationary surface 12. When the slit lamp 10 is not being used for an eye examination it may be secured to the axle 14 with a thumbscrew 20, which in turn prevents movement of the slit lamp at least in the fore-aft translational direction 13 and in a side-to-side translational direction 22.

Before an examination, the slit lamp 10 may be moved with the platform 12 to allow the patient access to an examination chair. Once seated, the slit lamp 10 may be adjusted for the particular patient. Because a base 24 of the slit lamp 10 is easily movable relative to the platform 12, the slit lamp 10 is generally locked into a static position on the platform 12 to prevent damage to the delicate slit lamp optical devices.

Thus, before and after each examination, the doctor usually has to manually manipulate the thumbscrew 20 to secure the slit lamp 10 in a desired position. Depending on the number of patients seen by the doctor, it may be necessary to manually manipulate (e.g., loosen or tighten) the thumbscrew 20 over thirty times in a single day. This repetitive task can fatigue the doctor's hand, and if forgotten may increase the likelihood for damage to or undesired movement of the slit lamp 10.

SUMMARY OF THE INVENTION

In one aspect of the present invention, a mechanism for securing a slit lamp includes a locking device for securing the slit lamp relative to at least two translational directions; a sensor configured to receive at least one type of a multimodal input from a user; and a controller in communication with the sensor, the controller operable to automatically direct the locking device to secure the slit lamp after a first multimodal input is detected by the sensor and operable to automatically direct the locking device to unsecure the slit lamp after as second multimodal input is detected by the sensor.

In another aspect of the present invention, a method for securing a slit lamp using an automated locking apparatus includes the steps of (1) activating a sensor proximate the slit lamp; (2) transmitting a signal from the sensor to a controller of the locking apparatus; and (3) providing a command from the controller to a locking mechanism, the command interpreted by the locking mechanism to secure or unsecure the slit lamp relative to at least two translational directions.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

At least one embodiment of the present invention is an apparatus that automatically locks or secures a slit lamp after each eye examination and unlocks it just before each examination. By way of example, the locking aspect of the apparatus may be achieved mechanically (e.g., a threaded rod), electromechanically (e.g., a solenoid), hydraulically, electromagnetically (e.g., an electromagnetic brake). In the illustrated embodiment, the apparatus takes the form of a threaded rod to replace the conventional thumbscrew, where the threaded rod is controlled by a motor and a controller located within a housing. A touch sensor on the housing communicates with the controller to activate the motor and cause the threaded rod to contact and thus secure the slit lamp relative to an axle before, during or after an examination.

Figure 2:
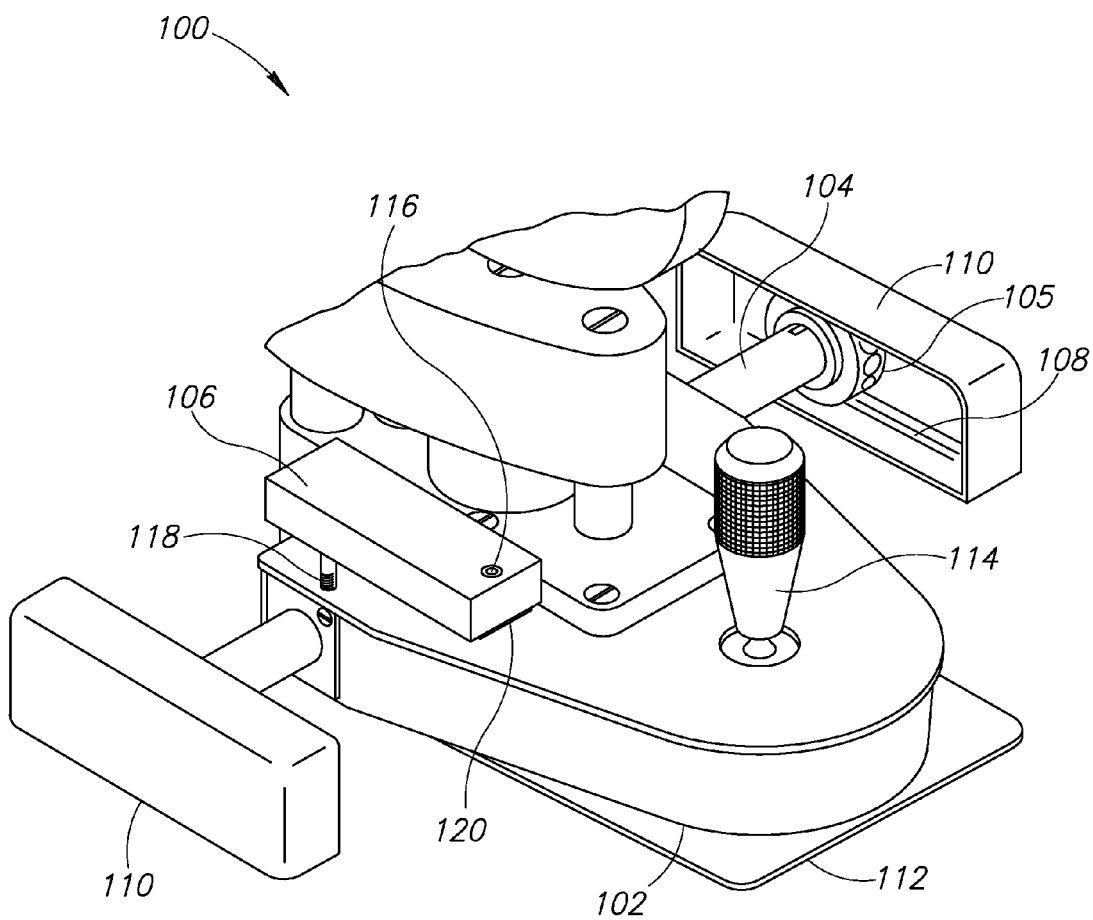
FIG. 2 is a partial perspective view of a slit lamp having a locking apparatus controllable to automatically secure the slit lamp to an axle according to an embodiment of the present invention.

FIG. 2 shows a slit lamp 100 with its base 102 securable to an axle 104 using an automated locking apparatus 106. The axle 104 is coupled to wheels 105, which engage or mesh with a track 108. The base 102 may be moved at least along two translational directions (e.g., fore-aft and side-o-side) relative to a stationary object such as track housings 110 or platform 112. The slit lamp 100 may be commanded to move along the axle 104 through operation of a joystick 114 or by manually applied forces. During, before or after an examination, the slit lamp 100 may be secured to or released from the axle 104 by touching a sensor 116 of the locking apparatus 106. As described in more detail below, the sensor 116 triggers a locking mechanism 118, which may take the form of a threaded rod, to move into a locked or unlocked position. The locking apparatus 106 may be bonded, adhered, fastened, or otherwise attached to the base 102 of the slit lamp 100. In the illustrated embodiment, the locking apparatus 106 is attached to the base 102 with an adhesive or bonding strip 120.

Figure 3:
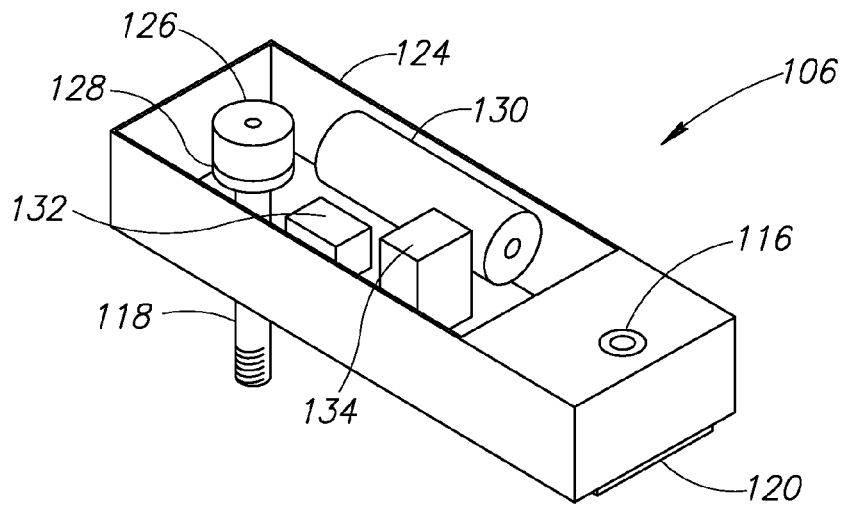
FIG. 3 is a schematic view of a locking apparatus for a slit lamp according to an embodiment of the present invention.
Figure 4:
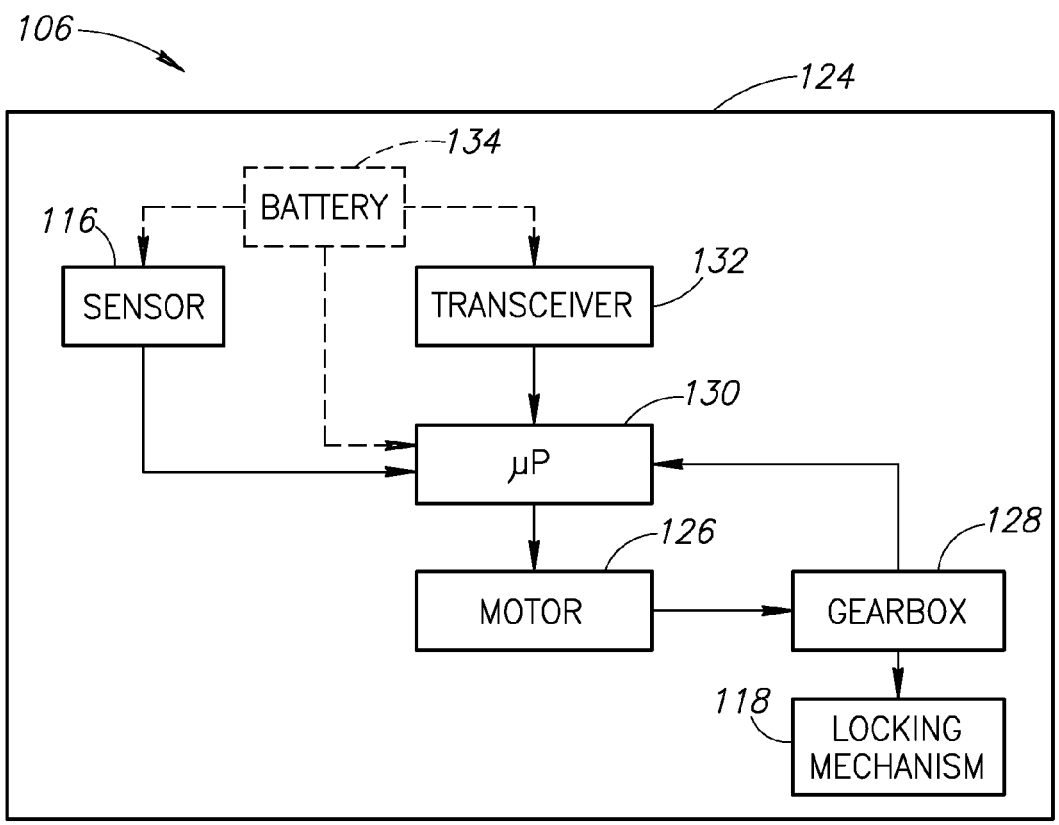
FIG. 4 is a block diagram of the locking apparatus of FIG. 3.

FIGS. 3 and 4 schematically show embodiments of the locking apparatus 106. More specifically, FIG. 3 shows the components of the locking apparatus 106 arranged in one possible mechanical layout while FIG. 4 shows the components arranged in a block diagram. The locking apparatus 106 includes a housing 124 supporting the sensor 116 and provides an opening for the locking mechanism 118.

In the illustrated embodiments, the housing 124 encloses a motor 126 coupled to a gearbox 128, which in turn is coupled to the locking mechanism (e.g., threaded rod) 118. A controller 130, which may take the form of a microprocessor, an open-loop controller, or a closed-loop controller, communicates with at least the motor 126 and the sensor 116. The motor 126 may take the form of a direct current (DC), alternating current (AC), or stepper motor. The latter may operate in conjunction with an open-loop controller to provide precise positioning of the locking mechanism 118. The sensor 116 may take the form of a capacitive touch sensor that is activated or otherwise triggered by human skin contact. Alternatively, the sensor 116 may take other forms, such as, but not limited to a pressure transducer, a resilient switch, a piezoelectric switch, etc. The sensor 116 activates the motor 126 by way of the controller 130 to rotate the locking mechanism 118 into a locked position relative to the axle 104. The sensor 116 may optionally activate a transceiver 132 through the controller 130 to power the slit lamp 100 from an OFF to an ON state, or vice-versa. The transceiver 132 may take the form of a radio transmitter, a radio receiver, or a non-radio, signal-transceiving device.

Figure 1:
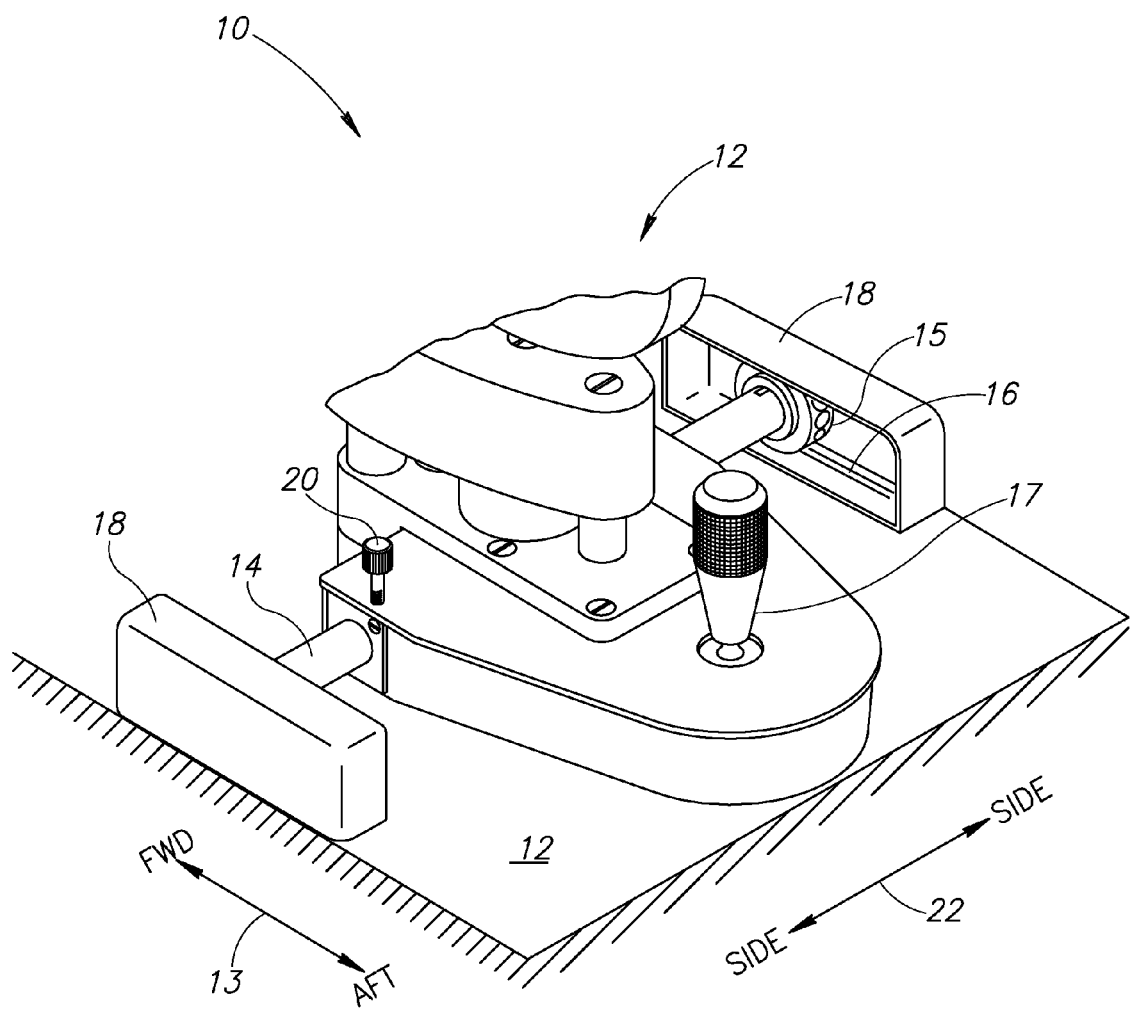
FIG. 1 is a partial perspective view of a conventional slit lamp having a thumbscrew for manually securing the slit lamp to an axle.

The locking mechanism 118 includes a threaded portion having the same thread pitch, diameter, and overall form as the conventional thumbscrew (FIG. 1). A non-threaded portion of the locking mechanism 118 may be fixed to the gearbox 128 or directly to the motor 126. The adhesive strip 120 operates to secure the locking apparatus 106 to the base 102 of the slit lamp 100 so that the locking apparatus 106 remains stationary even when subjected to vibrational loads or other loads that may be generated internally or externally with respect to the housing 124. A battery 134 may be located within the housing 124 to provide power to the sensor 116, the motor 126, the controller 130, or any combination thereof.

In one example of the locking apparatus 106 in operation, an eye doctor commences an eye examination by touching the sensor 116 to activate a counterclockwise rotation of the locking mechanism 118, which allows the slit lamp 100 to move freely along the axle 104. Touching of the sensor 116 also activates the transceiver 132 to power ON the slit lamp 100. Alternatively, powering ON the slit lamp 100 may automatically activate the locking mechanism 118. After the exam is complete, the doctor again touches the sensor 116 to initiate a clockwise rotation of the locking mechanism 118, which correspondingly secures the slit lamp 100 relative to the axle 104, thus preventing any undesired movement of the slit lamp 100. The after-exam touching of the sensor 116 may also activate the transceiver 132 to power OFF the slit lamp 100. Consequently, one touch of the sensor 116 turns ON and unlocks the slit lamp or turns OFF and locks the slit lamp.

In an alternate embodiment, activation of a fixation light, similar to the fixation light described in U.S. Pat. No. 7,549,748, may remotely trigger operation of the locking apparatus, where such triggering may be direct or by way of the controller. The remote triggering may take a variety of forms, such as, but not limited to, infrared, blue tooth, motion/vibration sensors, hard wiring, etc.

While the preferred embodiment of the invention has been illustrated and described, as noted above, many changes can be made without departing from the spirit and scope of the invention. By way of example, other embodiments of the locking mechanism may include an electromechanical solenoid, an electromagnetic brake, or a non-threaded mechanical clamp and any of these mechanisms may be hard wired or otherwise integrated into the slit lamp. For the purposes of the present invention, the locking mechanism should be broadly interpreted to include any device that may be configured to automatically prevent movement of the slip lamp relative to the axle such that the doctor or other personnel does not have to manually participate in such locking other than activating a switch or sensor (e.g., by touching, voice command, heat, proximity, etc.). Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A mechanism for securing a slit lamp, the mechanism comprising:
a locking device for securing the slit lamp relative to at least two translational directions;
a sensor configured to receive at least one type of a multi-modal input from a user; and
a controller in communication with the sensor, the controller operable to automatically direct the locking device to secure the slit lamp after a first multimodal input is detected by the sensor and operable to automatically direct the locking device to unsecure the slit lamp after a second multimodal input is detected by the sensor.

2. The mechanism of claim 1, wherein the translational directions include a fore-aft direction and a side-to-side direction.

3. The mechanism of claim 1, wherein the translational directions are orthogonal.

4. The mechanism of claim 1, further comprising a motor coupled to the locking device for moving the locking device between secured and unsecured positions as directed by the controller.

5. The mechanism of claim 1, wherein the locking device is a threaded rod.

6. The mechanism of claim 1, wherein the locking device is an electromagnetic brake.

7. The mechanism of claim 1, further comprising a gearbox driven by a motor, the gearbox configured to adjust a speed or direction of the locking mechanism.

8. The mechanism of claim 1, further comprising a transceiver configured to receive a signal to power the slit lamp to an on or off mode.

9. The mechanism of claim 8, wherein the transceiver includes a radio receiver.

10. The mechanism of claim 8, wherein the transceiver includes a radio transmitter.

11. The mechanism of claim 1, wherein the controller is a microprocessor.

12. The mechanism of claim 1, wherein the sensor is a capacitive touch sensor.

13. The mechanism of claim 1, further comprising a power source for supplying power to at least the motor.

14. The mechanism of claim 10, wherein the power source is a battery.

15. A method for securing a slit lamp using an automated locking apparatus, the method comprising:
activating a sensor proximate the slit lamp;
transmitting a signal from the sensor to a controller of the locking apparatus; and
providing a command from the controller to a locking mechanism, the command interpreted to automatically direct the locking mechanism to secure or unsecure the slit lamp relative to at least two translational directions based on the signal transmitted from the sensor.

16. The method of claim 15, further comprising changing a speed or direction of the locking mechanism with a gearbox interfaced between a motor and the locking mechanism.

17. The method of claim 15, wherein touching the sensor includes touching a capacitive touch sensor.

18. The method of claim 15, further comprising powering the slit lamp to be either on or off with a transceiver.

\* \* \* \* \*